United States Patent [19]

Davis

[11] Patent Number: 5,741,134
[45] Date of Patent: Apr. 21, 1998

[54] FILTER AND UNIVERSAL ADAPTER FOR USE WITH DENTAL ASPIRATOR TIPS

[75] Inventor: Ralph L. Davis, Genoa City, Wis.

[73] Assignee: Filtertek Inc., Hebron, Ill.

[21] Appl. No.: 479,135

[22] Filed: Jun. 7, 1995

[51] Int. Cl.⁶ .......................... A61C 17/06; A61C 17/14
[52] U.S. Cl. .................................... 433/91; 210/446
[58] Field of Search .......................... 433/91, 92, 95, 433/96, 25; 210/446, 447, 445, 448, 451, 437, 439

[56] References Cited

U.S. PATENT DOCUMENTS

| | | |
|---|---|---|
| 128,257 | 6/1872 | Synder . |
| 1,192,408 | 7/1916 | Frame . |
| 3,409,224 | 11/1968 | Harp et al. . |
| 3,476,144 | 11/1969 | Krantz .......................... 433/95 |
| 3,631,654 | 1/1972 | Riely et al. .......................... 210/446 |
| 3,890,712 | 6/1975 | Lopez . |
| 4,051,981 | 10/1977 | Mandlak . |
| 4,158,916 | 6/1979 | Adler . |
| 4,265,621 | 5/1981 | McVey . |
| 4,287,065 | 9/1981 | Raines .......................... 210/446 |
| 4,417,874 | 11/1983 | Andersson et al. . |
| 4,587,687 | 5/1986 | Ikonen et al. . |
| 4,690,757 | 9/1987 | Mathus et al. .......................... 210/446 |
| 4,852,564 | 8/1989 | Sheridan et al. . |
| 4,900,441 | 2/1990 | Graus et al. .......................... 210/446 |
| 5,076,787 | 12/1991 | Overmyer .......................... 433/95 |
| 5,078,603 | 1/1992 | Cohen . |
| 5,204,004 | 4/1993 | Johnston et al. .......................... 210/657 |
| 5,425,637 | 6/1995 | Whitehouse et al. . |
| 5,476,630 | 12/1995 | Orsing . |
| 5,547,375 | 8/1996 | Schneider . |

FOREIGN PATENT DOCUMENTS

| | | |
|---|---|---|
| 3316397.9 | 1/1985 | Germany . |
| WO 82/00764 | 3/1982 | WIPO . |
| WO 92/19437 | 11/1992 | WIPO . |

OTHER PUBLICATIONS

International Search Report dated Sep. 27, 1996 for PCT/US96/08999.

*Primary Examiner*—Nicholas D. Lucchesi
*Attorney, Agent, or Firm*—Brinks Hofer Gilson & Lione

[57] ABSTRACT

A filter-adapter for filtering amalgam and attaching multiple sizes of disposable aspirator tips to the suction line of a dental aspirator system is disclosed herein. The filter-adapter incorporates a filter for preventing amalgam from contaminating the suction line and significantly reducing the amount of amalgam that reaches the central amalgam separator in the system. The filter-adapter fits between the aspirator tip and the suction hose of the aspirator system. In particular, one embodiment of the filter-adapter comprises a substantially cylindrical, hollow body with a flowpath defined through the body, an outer surface diameter at one end sealably fitting one size aspirator tip and an inner surface diameter of the same end sealably fitting another size of aspirator tip, and a second end having an outer surface diameter sealably fitting the suction hose from the aspirator system. A substantially planar filter element is secured across the flowpath to prevent amalgam from entering the suction hose, and a ledge projects outwardly from the filter-adapter to prevent it from being drawn into the suction hose by vacuum pressure.

27 Claims, 4 Drawing Sheets

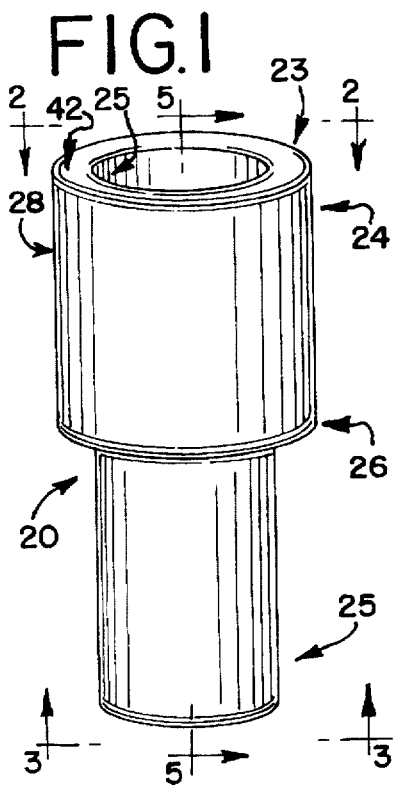
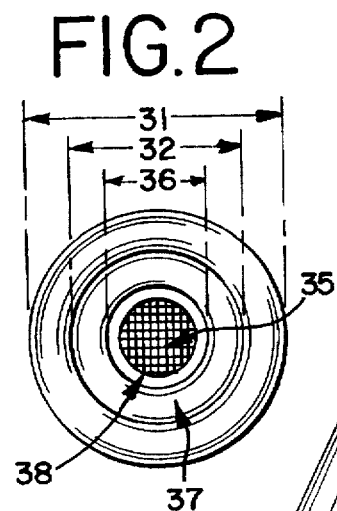
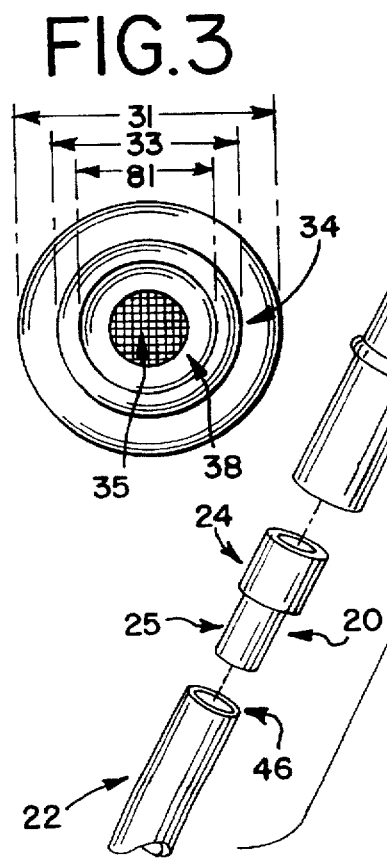
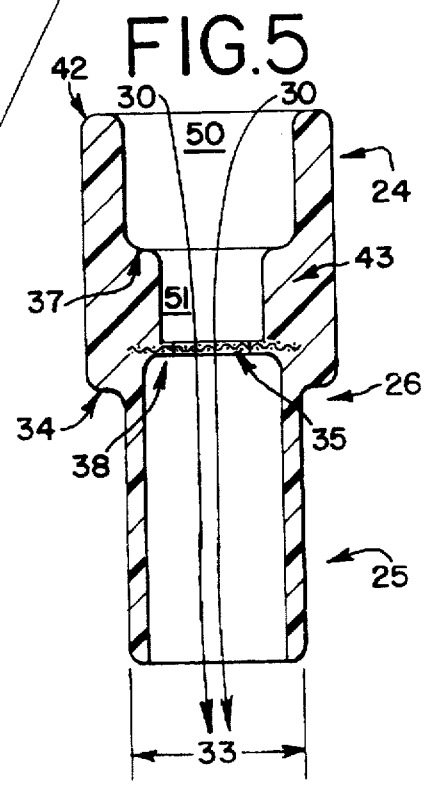

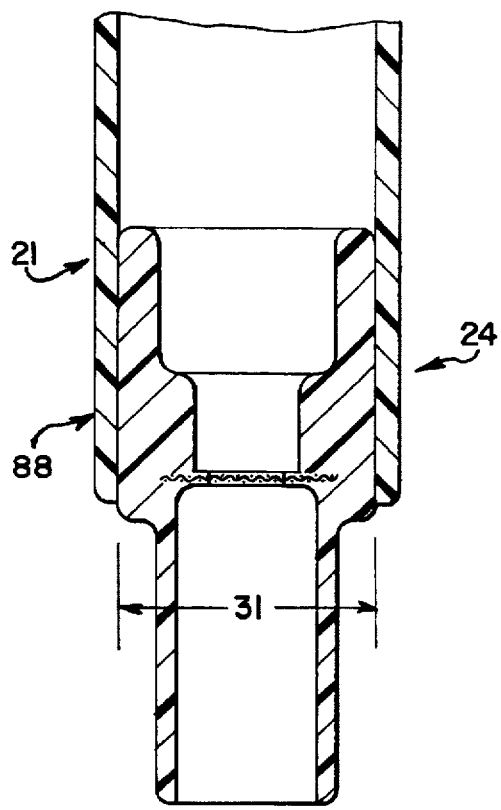
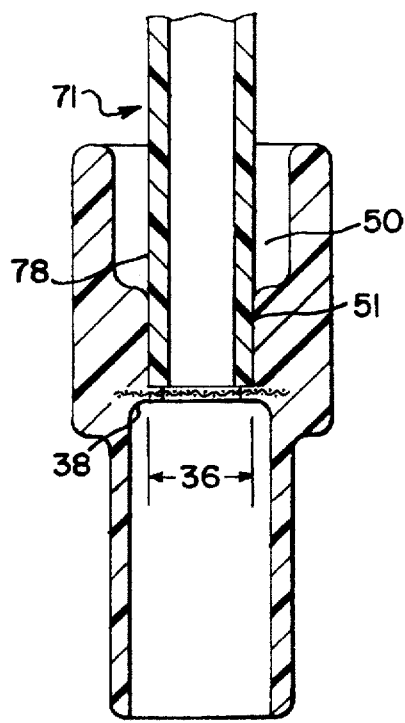
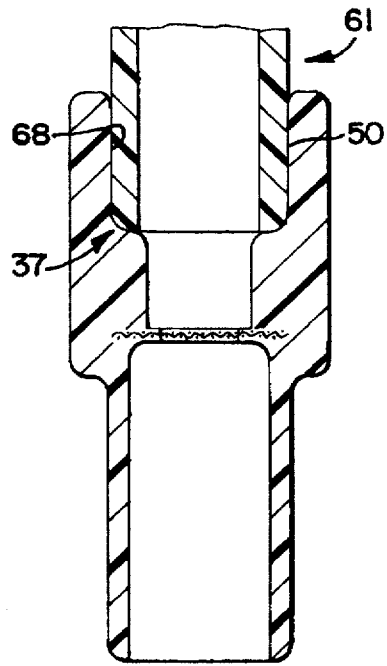
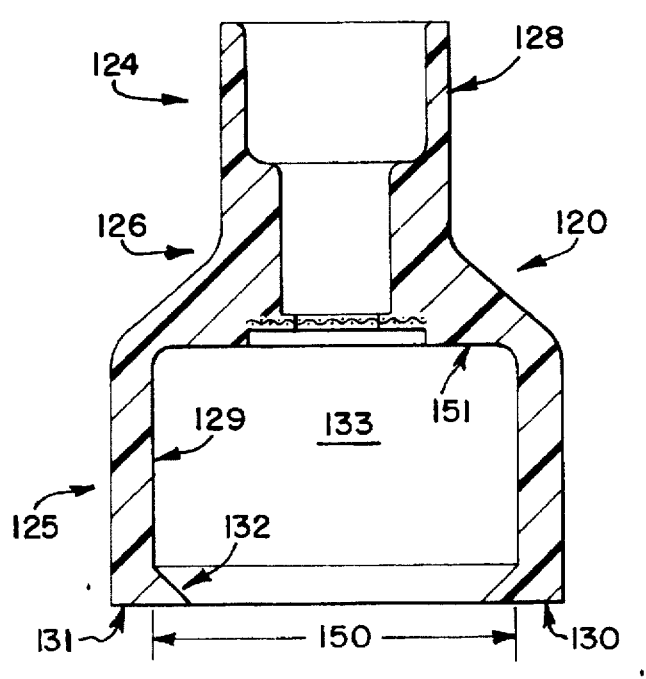

_PRIOR ART_
FIG. 11b
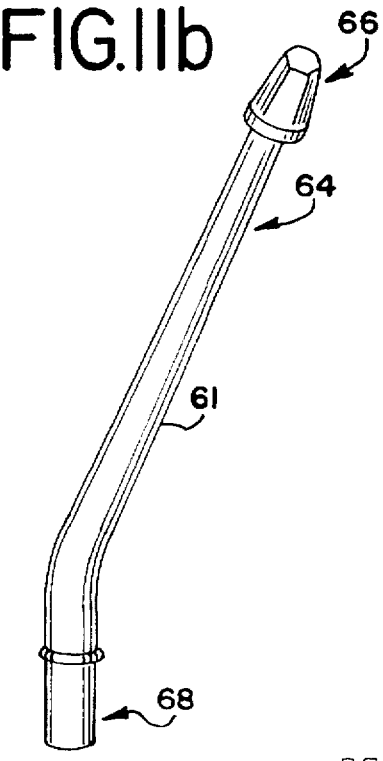
_PRIOR ART_
FIG. 11c
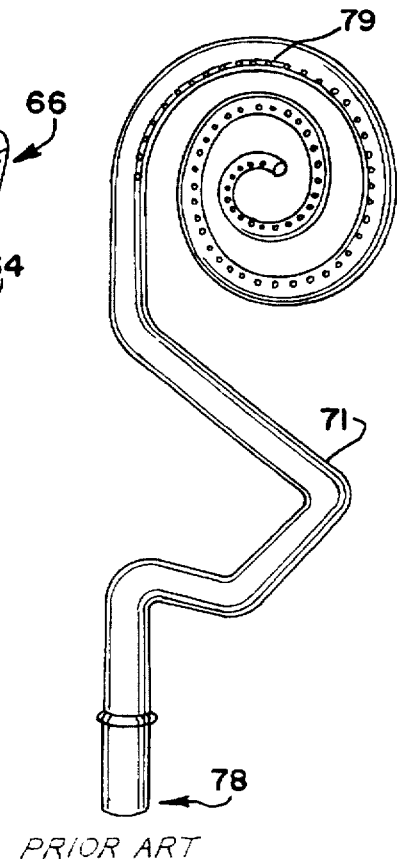
_PRIOR ART_

FILTER AND UNIVERSAL ADAPTER FOR USE WITH DENTAL ASPIRATOR TIPS

BACKGROUND OF THE INVENTION

The field of this invention relates to suction systems. More particularly, the invention relates to a filter and universal adapter for aspirator tips used in the dental field.

In the field of dentistry, an aspirator is used to remove saliva, water, and solid waste particles such as "amalgam" from the mouth of the patient during dental procedures. The aspirator is typically a hand-held, flexible suction hose attached to a powered suction system. Before using the aspirator on a patient, the dentist attaches either a high-speed suction tip or saliva ejector tip to the hand-held end of the suction hose. The tip is usually a sterile apparatus which is placed directly into the mouth of the patient during use. When the procedure has been completed, the tip is discarded.

High-speed suction tips and saliva ejector tips are available in several types and sizes. This assortment of tips is needed to accommodate the particular needs of various dental procedures. However, some of sizes will not fit a standard-sized suction hose on the dentist's aspirator system, thus limiting the choice of tips the dentist may use with his or her system. In particular, some of the tips have a cross-sectional diameter that is too wide or too narrow to be attached to the suction hose. While some tips are sold with adapters which remedy the lack of fit, these adapters are made to correspond with only one size of saliva ejector or suction tip. Thus, a variety of adapters must be kept on hand in order to ensure that the various tips can be used.

In general, aspirator systems can be difficult to maintain. Dental aspirators, for example, typically utilize an amalgam separator located near the centralized vacuum source of the system. The amalgam separator uses a mesh container or other filter media to prevent dental amalgam from exiting the system and contaminating water waste lines. The separator is cleaned often to remove the buildup of amalgam and must be disinfected between such cleanings. Infrequent cleaning or disinfecting of the separator can result in bacterial contamination of the suction lines in addition to the water waste lines. The contamination may subsequently reach the patient. This is unacceptable in the sterile environment dentistry demands.

To prevent excessive amounts of amalgam from reaching the central amalgam separator, some manufacturers of saliva ejector tips have incorporated small basket-type filters into their tips. These filters, however, are not effective to filter smaller-sized amalgam particles because the support structure for the filter has large openings. Furthermore, the filter basket cannot be used with differing sizes of saliva ejector tips or high-speed suction tips.

Therefore, there is a need for an inexpensive, sanitary, and easily accessible filtering device for preventing excessive build-up of amalgam within the amalgam separators in dental suction systems.

Furthermore, there is a need for a filter-adapter which allows a variety of high-speed suction tips and saliva ejector tips to be attached to a standard-sized suction hose in a dental aspirator system.

SUMMARY OF THE INVENTION

The preferred embodiment of the invention disclosed herein provides a disposable filter for connection between several sizes of dental aspirator tips and the suction hose of a dental aspirator system. Different types of tips may comprise a single size.

In one aspect of the present invention, the filter-adapter includes a substantially cylindrical, hollow body with a flowpath defined within the body. A substantially planar filter element is secured across the flowpath inside the filter-adapter to substantially prevent amalgam from entering the suction hose. A first end of the filter-adapter is configured to receive several sizes of the various disposable aspirator tips available. The first end has an outer surface diameter which can receive one size of disposable saliva ejector tip sealably fitting over the end of the filter-adapter. The first end of the filter-adapter also has an inner surface diameter which sealably fits to a smaller size of disposable saliva ejector tip into the interior of the filter-adapter. The opposite, or second end of the filter-adapter has an outer surface diameter configured so that the second end sealably fits inside a standard-sized suction hose from the suction system. A protruding ledge on the outside of the filter-adapter prevents it from being drawn into the suction hose.

In another aspect of the present invention, the first end of the filter-adapter is also supplemented by a smaller inner surface diameter located inside the middle portion of the filter-adapter. This smaller diameter is sized to receive a third size of disposable saliva ejector tip through the end of the connector. An inner ledge prevents the saliva ejector tip from being drawn through the filter-adapter or possibly harming the filter element.

In another aspect of the present invention, the second end of the filter adapter sealably fits over the terminus end of the suction hose.

In another aspect of the present invention, the filter-adapter is molded from a thermoplastic rubber compound to allow flexibility and a secure friction-fit of the various components to the filter-adapter. The filter element is preferably a nylon mesh screen molded into the sides of the filter-adapter.

In yet another aspect of the present invention, a dental aspiration system filters amalgam from a dental procedure using a filter-adapter sealably connected between an aspirator tip and the suction hose of the system.

These and other features and advantages of the invention will become apparent upon the review of the following detailed description of the presently preferred embodiments of the invention, taken in conjunction with the appended drawings.

BRIEF DESCRIPTION OF THE DRAWINGS

FIG. 1 is a perspective view of a first embodiment of the filter-adapter of the present invention.

FIG. 2 is a top plan view taken along line 2—2 of FIG. 1.

FIG. 3 is a bottom plan view taken along line 3—3 of FIG. 1.

FIG. 4 is a perspective view showing the filter-adapter of the present invention and its attachment to a suction hose and high-speed suction tip.

FIG. 5 is a cross-sectional view taken along line 5—5 of FIG. 1.

FIG. 6 is a cross-sectional view like FIG. 5 showing registration of the filter-adapter with a cross-sectional view of an outer diameter-fitting high-speed suction tip.

FIG. 7 is a cross-sectional view like FIG. 5 showing registration of the filter-adapter with a cross-sectional view of a first inner diameter-fitting saliva ejector tip.

FIG. 8 is a cross-sectional view like FIG. 5 showing registration of the filter-adapter with a cross-sectional view of a second inner diameter-fitting saliva ejector tip.

FIG. 9 is a cross-sectional view like FIG. 5, but of a second embodiment of a filter-adapter of the present invention.

DETAILED DESCRIPTION OF THE DRAWINGS AND PREFERRED EMBODIMENTS OF THE INVENTION

Figure 10:
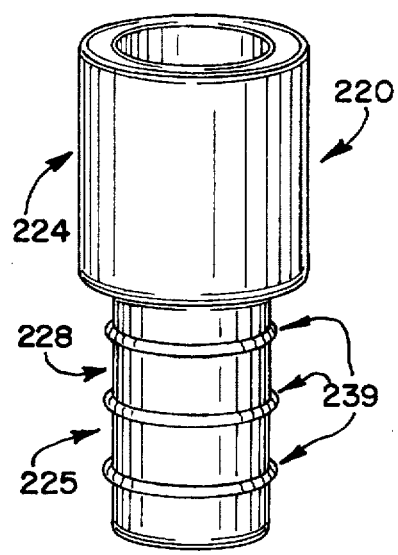
FIG. 10 is a perspective view of a third embodiment of the filter-adapter of the present invention.

A perspective view of a first preferred embodiment of the invention is shown in FIG. 1. Preferably, filter and universal adapter 20 includes a hollow body 23 of substantially cylindrical shape and circular cross-section. The body 23 has a first end 24, a second end 25, and a middle portion 26. Body 23 also has an outer surface 28 and an inner surface 29. The inner surface 29 defines a flowpath (represented by arrows 30) through the body 23 of filter-adapter 20.

Figure 14:
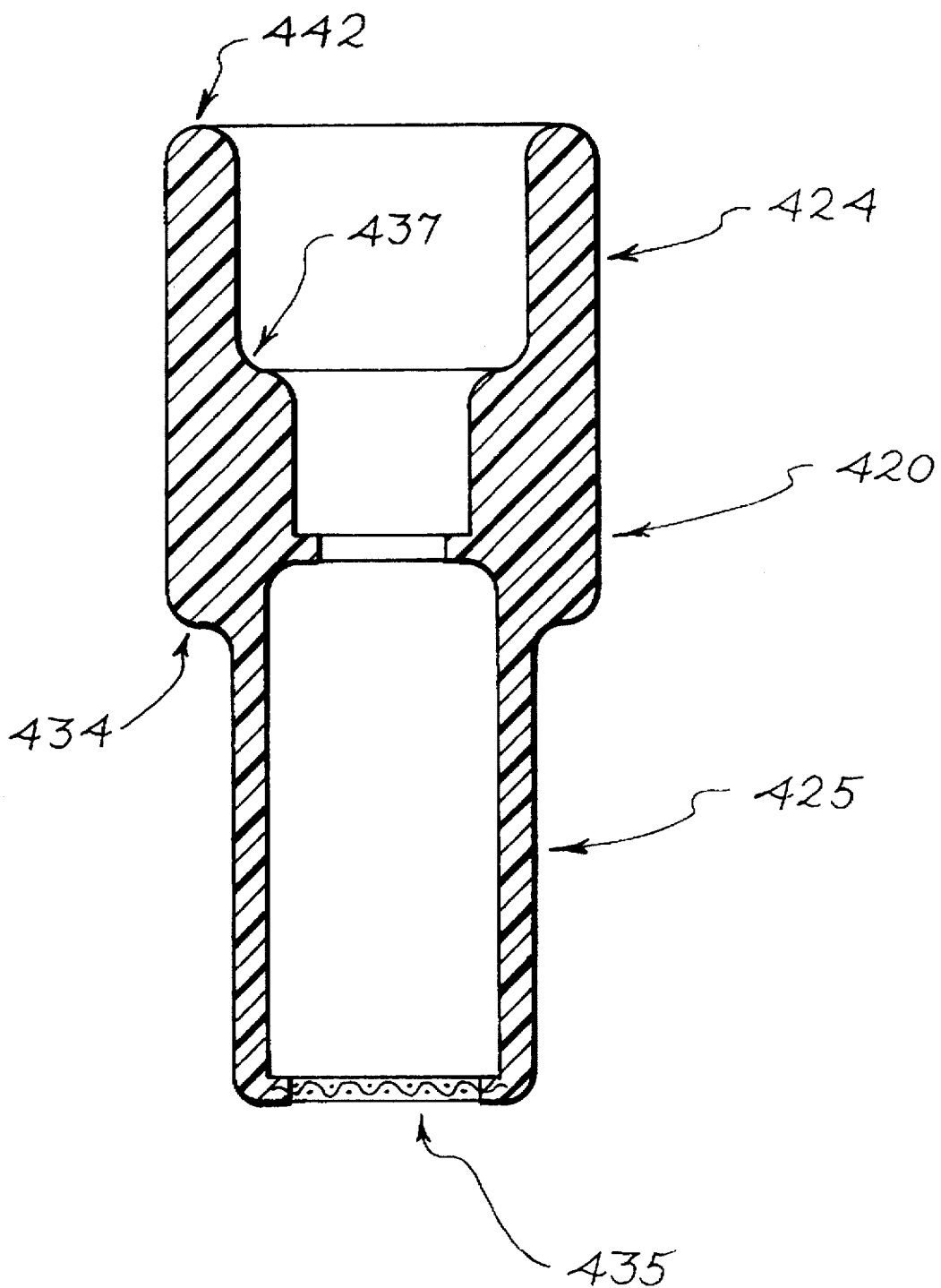
FIG. 14 is a cross-sectional view similar to FIG. 6 of another embodiment of the filter-adapter of the present invention.

A filter element 35, preferably comprising a mesh screen, is positioned to intersect flowpath 30 within the middle portion 26 of body 23. The cross-sectional view in FIG. 5 shows the filter element 35 mounted perpendicularly to flowpath 30. Filter element 35 is preferably made of woven nylon fiber, although molded plastic or woven metal wire are also contemplated. Filter element 35 is preferably molded to the inner surface 29 of the body 23 by insert injection molding. Note that the filter element 35 may be positioned anywhere within the flowpath 30, from the first end 24 through to the second end 25. This is illustrated in FIG. 14, which shows filter element 435 positioned at the second end 425 on filter-adapter 420 which is otherwise similar in configuration to the filter-adapter 20 shown in FIG. 6. Other corresponding parts of the filter-adapter 420 are indicated using similar numerals as in FIG. 6, plus four-hundred digits appended thereto.

Figure 11A:
FIGS. 11 (a) through (c) are perspective views of a high-speed suction tip and two types of saliva ejector tips.

FIGS. 11(a)-(c) illustrate three examples of aspirator tips manufactured by A. B. Kaltoplast. High-speed suction tip 21 is for example a SURG-O-VAC model used for general manual saliva aspiration of the oral cavity. Tip 21 comprises a tapered portion 81 and connecting end 88 for attachment to a suction hose. Saliva ejector tip 61 is a SCANFLEX model used for saliva removal while stationarily positioned within the oral cavity. The device comprises a flexible plastic tube 64 which includes a metal wire (not shown) molded along its length. The wire allows plastic tube 64 to retain its shape when bent to remain within a patient's mouth. Slotted end piece 66 prevents aspiration of the soft tissues of the mouth, and connecting end 68 is for attachment to a suction hose. Finally, saliva ejector tip 71 is used when more detailed shaping of the tip is desired for a particular dental procedure. Tip 71 comprises a thin length of wire-stiffened plastic tubing partially curled into a helical shape. Holes 79 are defined within the tip 71 to suction saliva through the sides of the tube. Saliva ejector tips 21, 61, and 71 each have connecting ends of different cross-sections and outside diameters.

FIG. 4 shows the positioning of the filter-adapter 20 in relation to hose 22 and disposable high-speed suction tip 21.

As shown in the figure, the second end 25 of body 23 is sized to accept the terminus end 46 of suction hose 22. The filter-adapter 20 filters the liquid and solid particles drawn by suction through the suction tip 21 during general dental procedures and substantially prevents amalgam from entering the suction hose 22.

Referring now to FIGS. 1–5, first end 24 of body 23 includes means for sealably fitting a variety of aspirator tips and is interfaceable with several sizes of aspirator tips such as those shown in FIGS. 11(a)-(c). Preferably, the first end 24 has an outer surface diameter 31 and a first inner surface diameter 32. Outer surface diameter 31 is sized so that the connecting end 88 of the high-speed suction tip of the type 21 shown in FIGS. 4 and 11(a) will fit over the outer surface diameter 31. FIGS. 4 and 6 show the registration of the elongated high-speed saliva ejector tip 21 with the outer surface diameter 31 of the first end 24 of filter-adapter 20.

In addition to the outer surface diameter 31, the first end 24 of the filter-adapter 20 is also configured to receive various sizes of saliva ejector tips into the interior of the filter-adapter 20. In particular, FIGS. 1, 2 and 5 show a first inner surface diameter 32 defined within first end 24 inside a first cavity 50. The first inner surface diameter 32 extends from the lip 42 of the first end 24 sufficiently into body 23 to allow a stable, frictional seal and grip on a saliva ejector tip inserted into cavity 50. The diameter of the flowpath 30 is reduced near the middle portion 26 of the body 23. As shown in FIGS. 2 and 5, ledge 37 is formed where flowpath 30 reduces to second inner surface diameter 36, which defines second cavity 51. First inner ledge 37 forms the junction between first cavity 50 and second cavity 51. Flowpath 30, having second inner surface diameter 36, continues through the middle portion 26 of body 23 until flowpath 30 intersects the filter element 35. FIG. 5 shows filter element 35 molded into the wall 43 of body 23. A second inner ledge 38 projects inwardly from wall 43 immediately adjacent to the filter element 35.

In this first preferred embodiment, the second end 25 fits within a standard-sized suction hose 22. Outer ledge 34 meets the lip of the suction hose terminus 46 to prevent the filter-adapter 20 from being drawn into the suction hose 22.

FIG. 6 illustrates the registration of high-speed suction tip 21 with the outer surface 28 of first end 24. As shown in the figure, connecting end 88 fits over first end 24 of filter-adapter 20 and is held frictionally in this position. Because the area of contact between the connecting end 88 and the outer surface 28 is relatively large, the filter-adapter 21 is resistant to being pushed too far into the tip 21.

The registrations of various sizes of disposable saliva ejector tips with the interior of the first end 24 of filter-adapter 20 are shown in FIGS. 7 and 8. In particular, FIG. 7 shows a SCANFLEX saliva ejector tip 61 (also shown in FIG. 11(b)) fitted within first cavity 50 of first end 24. The tip 61 is held within cavity 50 by friction, and first inner ledge 37 acts as a stop for the end 68 of the saliva ejector tip 61, preventing it from being inserted too far into the body 23 and possibly puncturing the filter element 35 and being drawn into suction hose 22.

FIG. 8 shows for example a Hygoformic curled saliva ejector tip 71 (also shown in FIG. 11(c)) fitted within second cavity 51 of first end 24. Similar to the attachment to first cavity 50, the tip 71 is held within cavity 51 by friction. Second inner ledge 38 prevents the saliva ejector tip 71 from puncturing filter element 35 and being drawn into suction hose 22.

In this first preferred embodiment, the outer surface diameter 31 is 0.310 inches, the first inner surface diameter 32 is 0.248 inches, and the second inner surface diameter 36 is 0.148 inches. The outer surface diameter 33 of second end 25 is 0.255 inches and has a wall thickness of 0.055 inches. First cavity 50 is 0.200 inches deep, measured from lip 42 to first inner ledge 37. Second cavity 51 is 0.200 inches deep, measured from first inner ledge 37 to second inner ledge 38. The connecting end 88 of high-speed suction tip 21 fits over the outside of first end 24, saliva ejector tip 61 fits within the first inner surface diameter 32 of first end 24, and curled saliva ejector tip 71 fits within the second inner surface diameter 36. Alternatively, the first inner surface diameter 32 may be 0.255 inches to accommodate only a saliva ejector tip 61.

A standard-sized suction hose from an aspirator system manufactured by various suppliers will fit over the outer surface diameter 33 second end 25. These dimensions have been found to provide secure fit and seal with the saliva ejector tips 21, 61 and 71 shown in FIGS. 11(a)–(c), while allowing ease of insertion and removal of the tips from the filter-adapter 20.

The measurements described herein do not limit the intended scope of the invention. Such measurements may vary to a wide degree depending on manufacturing tolerances and the fit acceptable for a particular type of saliva ejector tip or suction tube. Moreover, the flexibility of the material used for the filter-adapter may require variances in the measurements. The filter-adapter of the present invention can thus be constructed to fit a variety of tips, in many combinations. For example, in addition to the measurements listed above, the outer surface diameter 31 may be 0.365, 0.560, or 0.500 inches; the first inner surface diameter 32 may be 0.500, 0.440, 0.250, 0.255, or 0.450 inches; the second inner surface diameter 36 may be 0.440, 0.250, 0.150, or 0.155 inches; the outer surface diameter 33 of second end 25 may be 0.620, 0.430, or 0.435 inches; the inner surface diameter 81 of second end 25 may be 0.200, 0.370, or 0.500 inches. The depths of the various cavities can vary as well.

Of course, the overall shape of the filter-adapter of the present invention may vary depending on these measurements. Furthermore, junctures between ledges and walls of the filter-adapter may be rounded to a variety of radii, and wall thicknesses and ledge projections may vary in a large range.

FIG. 9 shows an alternative embodiment of a filter-adapter 120 with a second end 125 sealably fitting the terminus end 46 of suction hose 22. The terminus end 46 fits frictionally into the interior of the second end 125. The first end 124 has a configuration similar to filter-adapter 20 shown in the previous figures, and is thus connectable to various sizes of saliva ejector tips. To facilitate a tight fit and seal around the suction hose 22, a peripheral lip 131 extends inward from inner surface 129 at the edge 131 of second end 125. In this embodiment, second end 125 preferably has an inner surface diameter 125 of 0.500 inches, and the inner surface 129 of second 125 is 0.360 inches deep, measured from lip 131 to roof 151. The wall 130 of second end 125 has a thickness of 0.125 inches, and the peripheral lip 131 extends 0.125 inches from the inner surface 129 of second end 125.

Variations in measurements to accommodate other types and sizes of saliva ejector tips or high-speed suction tips are contemplated to be within the scope of this invention.

The filter-adapter 20 is preferably injection molded from a thermoplastic rubber material. In particular, a 64–73 durometer Santoprene® is preferred. Santoprene® thermoplastic rubber is manufactured by Monstanto Company, and available from Advanced Elastomer Systems, L.P., in St. Louis, Mo. The flexibility of this thermoplastic rubber material allows the filter-adapter 20 to fit securely to the saliva ejector tip 21 and suction hose 22 throughout most tolerance variations. The rubber material helps to preserve the vacuum in the dentist's aspirator system by creating an effective seal against leakage.

Finally, thermoplastic rubber is inexpensive enough to allow cost-effective disposability of the filter-adapter 20 after each use, thereby improving a sterile office environment. While Santoprene® is preferred, other rubber or plastic materials may be substituted.

To further promote the seal between the filter-adapter 20 (shown in FIGS. 1–8) and the suction hose 22, the outer surface 28 of second end 25 may be supplemented. Such an embodiment of a filter-adapter 220 is shown in FIG. 10. Preferably, this embodiment has a series of three spaced-apart ridges 239 molded to the outer surface 228 of second end 225. The ridges 239 improve the frictional grip between the outer surface 228 and the terminus end 46 of suction hose 22 by slightly enlarging the outer surface diameter and creating multiple seals. The resulting tight juncture improves the seal between the filter-adapter 220 and suction hose 22. Similarly, the embodiment shown in FIG. 9 can utilize a similar ridged structure on the inner surface 129 of second end 125 to promote the seal between the inner surface 129 and the outer surface of the terminus end 46 of suction hose 22.

The ridges in the preferred embodiment of FIG. 10 are preferably spaced apart approximately 0.08 inches from each other, and project from the outer surface 228 between 0.025 and 0.015 inches.

The ridges shown in FIG. 10 may also comprise tapered, angularly projecting ridges (not shown) from the outer surface 228 of second end 225. In such an embodiment, the cross section of each ridge (which extends circumferentially around the outer surface 228 similar to shown ridges 239) is triangular in shape, and the cross-sectional area of each ridge decreases with its distance from the middle of the filter-adapter. This tapering of the ridge size facilitates insertion of the filter-adapter into the suction hose. The angular projections, which themselves taper, hold more firmly to the walls of the outside-fitting suction hose. In this embodiment, the three ridges preferably project between 0.025 and 0.015 inches from the outer surface 228, with the projection length decreasing progressively away from the middle of the filter-adapter. The projecting point of each ridge preferably is spaced 0.08 inches from the point of the next ridge.

Figure 12:
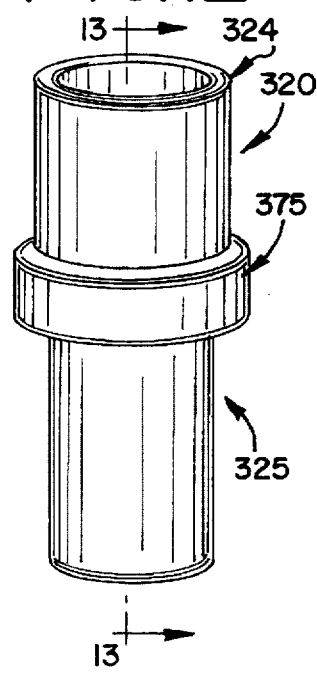
FIG. 12 is a perspective view of a fourth embodiment of the filter-adapter of the present invention.
Figure 13:
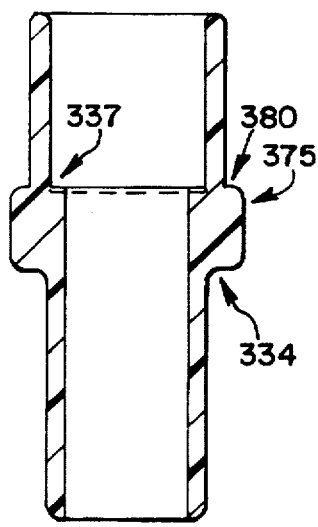
FIG. 13 is a cross-sectional view taken along line 13—13 of FIG. 12.

In order to better prevent a saliva ejector tip or a high-speed suction tip from being placed too far over the first end of the filter-adapter, a ledge may be placed near the first end of the filter-adapter. This embodiment is shown in FIGS. 12 and 13. Annular ring 375 is raised around the middle portion of the outside of connector 320, between first end 324 and second end 325. The ring 375 defines a first-end ledge 380 to prevent over-insertion of the filter-adapter into the interior of an outside-fitting saliva ejector tip or high-speed suction tip. Outer ledge 334 serves a similar function for a suction hose, and inner ledge 337 prevents over-insertion of an inside-fitting saliva ejector tip.

In this embodiment, ring 375 is preferably 0.325 inches wide, and preferably projects about 0.031 inches from the outer surface of first end 324.

The inexpensive filter-adapters described herein allow for use of a variety of disposable saliva ejector tips or high-speed suction tips with a convenient, disposable single-sized filter-adapter. Thus, the dentist does not need to stock a wide variety of adapters to fit each type of saliva ejector tip he or she wishes to use. Furthermore, the filter element integral in each filter-adapter traps most of the amalgam from a dental procedure and also allows most of the amalgam to be disposed of along with the filter-adapter and aspirator tip, thus preventing costly buildup within the central suction or amalgam separator system. These features promote cost efficiency and sterility in the dental office.

Of course, it should be understood that a wide range of changes and modifications can be made to the embodiments described above. For example, the filter element could have a shape other than planar and round. Also the filter element need not be perpendicular to the flow path. Furthermore, the shapes and configurations of the filter-adapter may vary with variations in the exemplary measurements described above. It is therefore intended that the foregoing detailed description be regarded as illustrative rather than limiting and that it be understood that it is the following claims, including all equivalents, which are intended to define the scope of this invention.

What is claimed is:

1. A filter-adapter device for connecting variable sizes of dental aspirator tips to a suction hose, said device comprising:
    a) a substantially cylindrical, hollow body having a first end, a second end, and a middle portion, said ends having a substantially circular cross-section, an outer surface, and an inner surface, said inner surface defining a flowpath through said body;
    b) said first end having an outer surface diameter adapted to sealably fit one of said sizes of aspirator tips and a first inner surface diameter adapted to sealably fit another one of said sizes of aspirator tips;
    c) said second end having an outer surface diameter adapted to sealably fit said suction hose and a ledge projecting from said outer surface, said ledge being of sufficient height to prevent said filter-adapter from being drawn through said suction hose;
    d) said middle portion including a second inner surface diameter smaller than said first inner surface diameter of said first end and located between the filter and said first inner surface diameter, said second inner surface diameter adapted to sealably fit another one of said sizes of aspirator tips through said first end;
    e) a substantially planar filter element secured across said flowpath between said middle portion and said second end; and
    f) an inner ledge projecting towards said flowpath from said inner surface of said middle portion, said inner ledge being of sufficient thickness to prevent an aspirator tip adapted to fit the inner surface diameter of said middle portion from being inserted from said first end through to said second end.

2. The device as recited in claim 1 wherein said ledges extend continuously around said inner surface.

3. The device as recited in claim 2 wherein said outer surface diameter of said first end is 0.36 inches, said first inner surface diameter of said first end is 0.24 inches, said outer surface diameter of said second end is 0.25 inches, and said second inner surface diameter of said middle portion is 0.14 inches.

4. The device as recited in claim 1 wherein said filter-adapter is comprised of a thermoplastic having a durometer of between about 64 and about 73.

5. The device as recited in claim 4 wherein said filter-adapter is comprised of thermoplastic rubber.

6. The device as recited in claim 1 wherein said filter element further comprises a mesh screen.

7. The device as recited in claim 6 wherein said filter element is comprised of nylon.

8. The device as recited in claim 7 wherein said filter element is secured to the inner surface of said middle portion.

9. The device as recited in claim 1 wherein said filter element is secured to said second end.

10. The device as recited in claim 1 wherein said second end further comprises a plurality of ridges extending from said outer surface of said second end for frictionally securing said suction hose to said second end.

11. The device as recited in claim 10 wherein said ridges extend circumferentially around said second end.

12. The device as recited in claim 1 wherein said filter-adapter further comprises molded plastic.

13. The device as recited in claim 1 wherein said suction hose has a terminus end, and said second end is adapted to sealably fit over said terminus end.

14. The device as recited in claim 1 wherein said suction hose has a terminus end, and said second end is adapted to sealably fit inside said terminus end.

15. A device for connecting and interchanging at least two dental aspirator tips having different cross-sectional diameters to a suction source, said device comprising:
    a) an adapter having a hollow body having a first end and a second end, said body defining a flowpath therethrough, said second end adapted to sealably fit a suction hose;
    b) a substantially planar filter element secured across said flowpath; and
    c) means on said first end for sealably fitting at least two different sizes of dental aspirator tips, said tips each having different cross-sectional diameters.

16. The device of claim 15 wherein said body further comprises an outer surface and a ledge projecting from said outer surface, said outer surface adapted to sealingly fit within said suction hose, and said ledge of sufficient height to prevent said device from being drawn through said suction hose.

17. The device of claim 15 wherein said device is comprised of thermoplastic.

18. The device of claim 17 wherein said device is comprised of a thermoplastic having a durometer of between about 64 and 73.

19. The device of claim 15 wherein said filter element comprises a nylon mesh.

20. The device of claim 15 wherein said means on said first end for sealably fitting at least two different sizes of dental aspirator tips includes:
    a first inner surface diameter portion adapted to sealably fit one of said sizes of tips; and
    a second inner surface diameter portion adapted to sealably fit another one of said sizes of tips.

21. The device of claim 15 wherein said means on said first end for sealably fitting at least two different sizes of dental aspirator tips includes:
    an inner surface diameter portion adapted to sealably fit one of said sizes of tips; and
    an outer surface diameter portion adapted to sealably fit another one of said sizes of tips.

22. A device for connecting and interchanging at least two dental aspirator tips having different cross-sectional diameters to a suction source, said device comprising:

a filter-adapter device formed by injection molding thermoplastic to a filter element to form a monolithic body around said filter element, said body having a first end and a second end and including a flowpath defined from said first end through said filter element and through said second end, said first end adapted to sealingly fit a suction hose and said second end adapted to fit at least two different sizes of aspirator tips.

23. The device of claim 22 wherein said thermoplastic has a durometer of between about 64 and about 73.

24. The device of claim 22 wherein said second end includes an outer surface and a ledge projecting from said outer surface, said ledge of sufficient height to prevent said device from being drawn through said suction hose.

25. A method of using a dental aspirator system, said method comprising the steps of:
   a) providing a suction hose;
   b) attaching an adapter to said suction hose, said adapter having a first end adapted to sealably fit at least two different sizes of aspirator tips and a second end adapted to sealably fit said suction hose, said adapter defining a flowpath between said first end and said second end and including a substantially planar filter element secured across said flowpath;
   c) attaching a first aspirator tip to said second end of said adapter, said first aspirator tip having a first cross-sectional diameter; and
   d) changing the aspirator tip attached to the suction hose to a second aspirator tip having a cross-sectional diameter different from said first cross-sectional diameter by either
      i) removing said first aspirator tip from said adapter and attaching said second aspirator tip to said second end of said adapter; or
      ii) removing the adapter from the suction hose and attaching a second but identical adapter to the suction hose and attaching said second aspirator tip to the second end of the second adapter.

26. A method of filtering amalgam in a dental suction system, said method comprising the steps of:
   a) providing a suction hose;
   b) providing an adapter having a first end and a second end, said first end of said adapter having a first end including an outer surface diameter adapted to sealably fit one size of an aspirator tip and a first inner surface diameter adapted to sealably fit another size of an aspirator tip, said second end of said adapter adapted to sealably fit said suction hose, said adapter defining a flowpath between said first and second ends of said adapter and including a filter element secured across said flowpath;
   c) attaching said second end of said adapter to said suction hose; and
   d) attaching an aspirator tip onto said second end of said adapter, a portion of said aspirator tip being positioned over said outer surface diameter of said adapter.

27. A method of manufacturing a filter-adapter device for connecting dental aspirator tips to a suction hose, said method comprising the steps of:
   a) providing a substantially planar filter element; and
   b) injection molding a thermoplastic to said filter element to form a monolithic body around said filter element, said body having a first end and a second end and including a flowpath defined from said first end through said filter element and through said second end, said first end adapted to sealingly fit said suction hose and said second end adapted to fit at least two different sizes of said aspirator tips.

* * * * *